United States Patent
Reischl et al.

(10) Patent No.: US 6,506,164 B2
(45) Date of Patent: Jan. 14, 2003

(54) DEVICE FOR ELECTROMECHANICAL STIMULATION AND TESTING OF HEARING

(75) Inventors: Gabriele Reischl, Munich (DE); Hans Leysieffer, Taufkirchen (DE); Gerd M. Müller, Lohhof (DE)

(73) Assignee: Phonak AG, Stafa (CH)

( * ) Notice: Subject to any disclaimer, the term of this patent is extended or adjusted under 35 U.S.C. 154(b) by 24 days.

(21) Appl. No.: 09/813,443

(22) Filed: Mar. 22, 2001

(65) Prior Publication Data

US 2001/0025148 A1 Sep. 27, 2001

(30) Foreign Application Priority Data

Mar. 22, 2000 (DE) .......................................... 100 14 200

(51) Int. Cl.[7] .................................................. A61B 5/00
(52) U.S. Cl. ...................................... 600/559; 128/246
(58) Field of Search ................................. 600/559, 300, 600/25; 606/129; 128/246

(56) References Cited

U.S. PATENT DOCUMENTS

| | | |
|---|---|---|
| 5,776,144 A | 7/1998 | Leysieffer et al. |
| 5,788,711 A * | 8/1998 | Lehner et al. ................. 600/25 |
| 5,833,626 A | 11/1998 | Leysieffer |
| 6,113,531 A * | 9/2000 | Leysieffer et al. ............ 600/25 |

OTHER PUBLICATIONS

"Ein vollständig implantierbares Hörsystem für Innenhoschwerhörige: TICA LZ 3001" [A totally implantable hearing device for the treatment of sensorineural hearing loss: TICA LZ 3001] by H. Leysieffer et al.; HNO, vol. 46, Oct. 1998; pp. 853–863.

"Elektronische Hörimplantate bei Innenohrschwerhörigkeiten"[An implantable piezoelectric hearing aid transducer for sensorineural hearing loss] by H. Leysieffer et al.; Parts I and II, HNO, vol. 45, Oct. 1997; pp. 792–815.

* cited by examiner

*Primary Examiner*—Willis R. Wolfe
*Assistant Examiner*—Mahmoud Gimle
(74) *Attorney, Agent, or Firm*—Nixon Peabody LLP; David S. Safran

(57) ABSTRACT

Device for electromechanical stimulation and testing of the hearing, including an electromechanical transducer for producing mechanical vibrations, a mechanical coupling element for transmitting mechanical stimulation vibrations from the electromechanical transducer without surgery through the external auditory canal to the umbo, and thus, to the manubrium malleli of the ossicular chain, a positioning device for positioning the coupling element with reference to the umbo, and a fixing device for secure, play-free linkage of the positioning device to human body, especially the human skull. An intermediate element is provided between the positioning device and the electromechanical transducer, said intermediate element being designed and dimensioned such that the intermediate element transmits quasi-steady-state positioning adjustments from the positioning device to the transducer, but reduces transmission of at least dynamic forces from the positioning device to the coupling element at least to such an extent that the risk of middle or inner ear damage is substantially reduced.

4 Claims, 1 Drawing Sheet

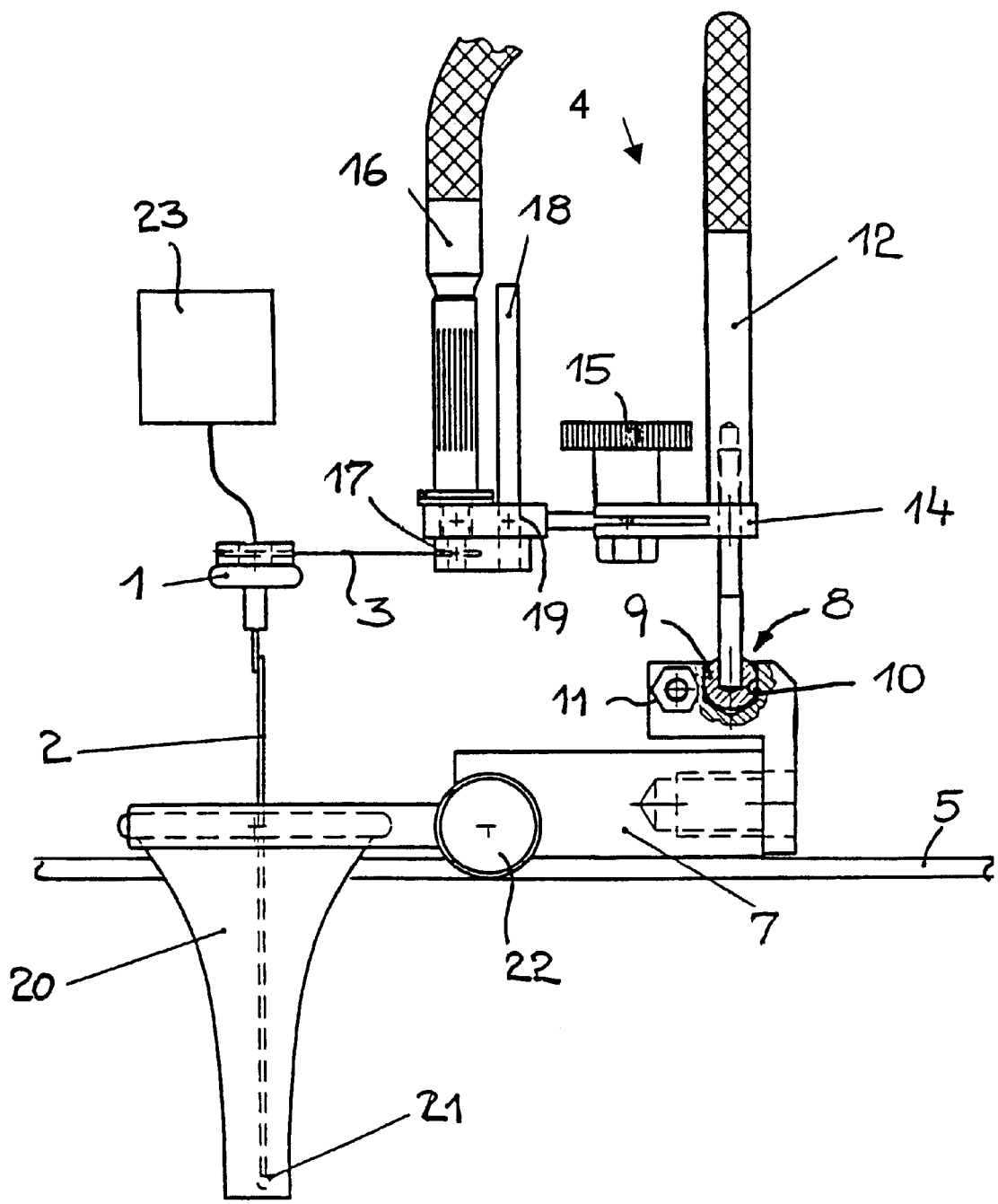

DEVICE FOR ELECTROMECHANICAL STIMULATION AND TESTING OF HEARING

BACKGROUND OF THE INVENTION

1. Field of the Invention

The invention relates to a device for electromechanical stimulation and testing of hearing, comprising an electromechanical transducer for producing mechanical vibrations, a mechanical coupling element for transmitting mechanical stimulation vibrations from the electromechanical transducer without surgery through the external auditory canal to the umbo and thus to the manubrium mallei of the ossicular chain, positioning means for positioning the coupling element with reference to the umbo, and fixing means for secure, play-free linkage of the positioning means to the human body, especially the human skull.

2. Description of Related Art

A device for electromechanical stimulation and testing of hearing is known from U.S. Pat. No. 5,833,626. A positioning means suitable for this purpose is detailed in U.S. Pat. No. 5,776,144. Such a device makes it possible to demonstrate pre-operatively in a noninvasive manner, i.e., without surgery, to the test subject awaiting implantation the improvement of hearing and sound quality. This improvement can be expected by the use of a partially or fully implantable hearing system which stimulates the middle or inner ear with mechanical vibrations by being coupled to an electromechanical transducer. A fully implantable hearing system of this type is described, among others, in the paper of H. Leysieffer, et al., "A totally implantable hearing device for the treatment of sensorineural hearing loss: TICA LZ 3001," HNO, vol. 46, October 1998, pages 853 to 863.

The positioning means makes it possible to precisely route to the destination the acting end of the mechanical coupling element, for example a coupling rod which is connected to the electromechanical transducer. A fixing means fixes the spatial position between the positioned coupling element and the umbo. Practical experience has shown that a certain risk exists in using the device. The positioning and/or fixing means may be accidentally touched and moved. The tympanic membrane or the ossicular chain can be damaged, or pressure can be exerted on the inner ear and the semicircular ducts. This can lead to vertigo or even hearing loss. This risk also exists for spontaneous head movements of the test subject.

SUMMARY OF THE INVENTION

A primary object of the present invention is to further increase the safety of a device of the initially mentioned type.

According to the invention, this and other objects are achieved by a device such that, between the positioning means and the electromechanical transducer there is an intermediate element which is designed and dimensioned such that it transmits quasisteady-state positioning adjustments from the positioning means to the electromechanical transducer, but reduces transmission of at least dynamic forces from the positioning means to the coupling element at least to such an extent that the risk of middle or inner ear damage is substantially reduced.

In the stimulation and testing device of the invention, the transducer together with the coupling element follows the relatively slow position changes which are called quasisteady-state here and which are caused by the actuation of the positioning means. The physician can thus guide the active end of the coupling element precisely and free of relative movements to structures in the human body, especially to the umbo, as the target point. Conversely, in the case of an unintentional external action which generally takes place by jerks and jolts, for example by hitting the positioning means with the hand, an instrument or the like, the dynamic forces acting on the positioning means are kept away from the transducer and the coupling element at least to a substantial extent.

The intermediate element may be made as a spring member, which is a structurally simple approach. Here, the spring member, electromechanical transducer and coupling element from a spring/mass system which preferably has a natural frequency in the range from 0.5 to 5 Hz.

The spring member can consist of one or more flexional springs. The springs may be simple flexional springs.

Preferably, the coupling element is made as a coupling rod, and the spring member is aligned at least roughly perpendicular to the longitudinal axis of the coupling rod.

These and further objects, features and advantages of the present invention will become apparent from the following description when taken in connection with the accompanying drawing which, for purposes of illustration only, shows a single embodiment in accordance with the present invention.

BRIEF DESCRIPTION OF THE DRAWINGS

The sole FIGURE of the drawings shows a schematic view of the stimulation and testing device of the invention.

DETAILED DESCRIPTION OF THE INVENTION

With reference to the drawing, the device comprises an electromechanical transducer 1, the output side of which is fixedly connected to a coupling element which is designed as a rigid coupling rod 2. The transducer 1 is connected via an intermediate element 3 to a positioning means 4. The positioning means 4 in turn is attached to a fixing means which is only schematically shown at 5 and which makes it possible to link the positioning means 4 to the human body, especially to the human skull, securely and without play.

The illustrated positioning means 4 is provided with a base 7 which is coupled to the fixing means 5. The base 7 carries a clampable ball joint 8 which has a ball 9 and an associated ball receiver 10. By means of an adjusting screw 11, the ball joint 8 can be locked in a position which can be set by means of an adjustment rod 12 which is fixedly connected to the ball 9. A transversely extending support arm 14 the length of which is adjustable is attached to the adjustment rod 12. The adjusted length of the support arm 14 is fixed by means of a clamping screw 15. A linear adjustment device 16 engages the end of the support arm 14 which is remote from the adjustment rod. This device is connected on its end which is the bottom end in the figure to a slide 17 to which a guide pin 18 is attached. The guide pin 18 is movably guided in a hole 19 of the support arm 14 in a direction which is essentially parallel to the longitudinal axis of the coupling rod 2. The transducer 1 is connected to the slide 17 via the intermediate element 3. By means of the linear adjustment device 16 the transducer 1 can be sensitively adjusted via the slide 17 and the intermediate element 3 in the longitudinal direction of the coupling rod 2. The linear adjustment device 16 preferably includes a hydraulic piston/cylinder arrangement which is not shown in detail and which, upon actuation, on its end which is remote from the transducer 1, allows fine adjustment of the transducer 1 together with the coupling rod 2 relative to the support arm 14 in the position which is essentially perpendicular to the latter.

Furthermore, an ear speculum 20 is attached to the base 7 in an easily removable manner. To secure and release the ear speculum 20 a clamp 22 which interacts with the base 7 and the ear speculum 20 is used. The ear speculum 20 accommodates the part of the coupling rod 2 remote from the transducer 1, wherein the longitudinal axis of the coupling rod 2 can be aligned with the longitudinal axis of the ear speculum. Optionally, the ear speculum 20 can be primarily supported on the base 7 to compensate for small spatial angles.

When the device is used, the ear speculum 20, with visual monitoring, if necessary with the aid of a microscope, is inserted into the external auditory canal of the test subject. In the suitable position, the base 7 is fixed with reference to the skull of the test subject by the fixing means 5. The fixing means 5 can, for example, be made as a head support for bilateral, pain-free attachment in the ear area in the manner known from FIG. 4 of U.S. Pat. No. 5,776,144 and on the side of the skull opposite the ear speculum 20 can have a molded part which, at the second support surface, surrounds the external ear which is located there. But, among others, there can also be a correspondingly adapted helmet as the fixing means 5 to which the base 7 of the positioning device 4 is attached.

When the ball joint 8 is unclamped, the linear adjustment device 16 can be turned around the center of the ball 9 in all three rotational spatial degrees of freedom. The mutual distance of the longitudinal axes of the adjustment rod 12 and the coupling rod 2 can be adjusted when the clamping screw 15 is loosened. By attaching the fixing means 5 to the body of the test subject, positioning of the system attached to the fixing means, subsequent clamping of the clamping screws 11 and 15 and corresponding adjustment of the linear adjustment device 16 is possible. Thus, exact, play-free positioning of the free acting end 21 of the coupling rod 2 relative to the umbo as the target point on the body is possible, wherein the free acting end 21 preferably is spherical. The position of the free acting end 21 can be checked, for example, by a microscope. The mutual offset of the coupling rod 2 and the positioning means 4 ensures that the optical axis of the microscope or the naked eye of the physician is not covered by the positioning system itself or its components.

Stimulation takes place by a signal generator which is shown schematically at 23 delivering electrical signals to the electromechanical transducer, and by the transducer 1 via the coupling rod 2 exciting the umbo to mechanical vibrations. The transducer 1 can thus preferably correspond to the electromechanical transducer of the hearing system to be implanted. One example of a suitable electromechanical transducer is described in detail in the papers of H. Leysieffer, et al., "An implantable piezoelectric hearing aid transducer for sensorineural hearing loss," Parts I and II, HNO, vol. 45, October 1997, pages 792 to 815.

In the illustrated embodiment, the intermediate element 3 consists of two simple flexional springs arranged in parallel, of which in the figure only one can be seen, while the other extends offset normal to the plane of the figure and behind the spring to be seen. The intermediate element 3, the electromechanical transducer 1, and the coupling rod 2 form a spring/mass system which is preferably designed such that it has a natural or resonant frequency (or, in the case of several natural frequencies, a lowest first natural frequency) in the range from 0.5 to 5 Hz. In this way, dynamic forces having a frequency higher than this natural frequency (such forces can occur, for example, by accidental impacts against the positioning means 4), are transmitted, if at all, only substantially and are attenuated from the positioning means 4 to the coupling rod 2. The coupling rod 2, however, normally follows the quasisteady-state positioning adjustments of the positioning means 4. If, however, the transducer 1, during positioning, inadvertently comes too close to the target point, the flexional springs which form the intermediate element 3 can deflect and in this way, also counteract damage to the middle and/or inner ear.

The intermediate element 3 may basically also be constructed in a different manner. For example, the intermediate element 3 may comprise a force limiter, for example in the form of a friction or induction coupling, which allows transmission of forces only up to a predetermined upper limit.

While a single embodiment in accordance with the present invention has been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. Device for electromechanical stimulation and testing of the hearing, comprising:

an electromechanical transducer for producing mechanical vibrations, a nonsurgical mechanical coupling element for transmitting mechanical stimulation vibrations from the electromechanical transducer through the external auditory canal to the umbo and to the manubrium mallei of the ossicular chain;

positioning means for positioning the coupling element with reference to the umbo; and fixing means for secure, play-free linkage of the positioning means to the human body;

wherein a spring member is provided between the positioning means and the electromechanical transducer, said spring member being configured and dimensioned for transmitting quasi-steady-state positioning adjustments from the positioning means to the electromechanical transducer, and wherein the spring member, the electromechanical transducer and the coupling element form a spring-mass system which has a natural frequency in the range from 0.5 to 5 Hz for sufficiently reducing transmission of at least dynamic forces from the positioning means to the coupling element to an extent that the risk of middle or inner ear damage is substantially reduced.

2. Device as claimed in claim 1, wherein the spring member comprises at least one flexional spring.

3. Device as claimed in claim 2, wherein the spring member comprises at least one simple flexional spring.

4. Device as claimed in claim 3, wherein the coupling element is a coupling rod and the spring member is aligned at least roughly perpendicular to the longitudinal axis of the coupling rod.

* * * * *